US00PP12675P2

(12) United States Plant Patent
van den Bosch

(10) Patent No.: US PP12,675 P2
(45) Date of Patent: Jun. 4, 2002

(54) HYPERICUM PLANT NAMED 'BOSANEY'

(75) Inventor: Bernard Renee van den Bosch, Rijnsburg (NL)

(73) Assignee: H. & B.R. van den Bosch B.V., Rijnsburg (NL)

( * ) Notice: Subject to any disclaimer, the term of this patent is extended or adjusted under 35 U.S.C. 154(b) by 0 days.

(21) Appl. No.: 09/592,375

(22) Filed: Jun. 12, 2000

(51) Int. Cl.[7] ..... A01H 5/00
(52) U.S. Cl. ..... Plt./226
(58) Field of Search ..... Plt./263, 226

(56) References Cited

U.S. PATENT DOCUMENTS

PP568 P * 3/1943 Grullemans ..... Plt./226
PP10,979 P * 6/1999 van den Bosch ..... Plt./226
PP10,994 P * 7/1999 van den Bosch ..... Plt./226
PP11,619 P * 11/2000 van den Bosch ..... Plt./226

OTHER PUBLICATIONS

GTITM UPOVROM Citation for 'Bosaney' as per NI PBR SJK0023; May 6, 1998.*
GTITM UPOVROM Citation for 'Bosaney' as per QZ PBR 981431; Oct. 13, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Hypericum plant named 'Bosaney', characterized by its medium to late flowering; long stem length; medium-sized light orange red-colored berries; and excellent post-production longevity.

2 Drawing Sheets

BACKGROUND OF THE INVENTION

The present Invention relates to a new and distinct cultivar of Hypericum plant, botanically known as *Hypericum androsaemum*, commercially used as a cut flower, and hereinafter referred to by the name 'Bosaney'. The new Hypericum does not have any medicinal value.

The new Hypericum is a product of a planned breeding program conducted by the Inventor in Rijnsburg, The Netherlands. The objective of the breeding program was to develop cut Hypericum varieties with large berries, attractive berry color and long flowering stem length.

The new cultivar originated from a cross made by the Inventor in 1988 of two proprietary selections. The female, or seed, parent was identified as code number 93 and the male, or pollen, parent was identified as code number 71. The cultivar Bosaney was discovered and selected by the Inventor in 1994 as a flowering plant within the progeny of the stated cross in a controlled environment in Zimbabwe.

Asexual reproduction of the new Hypericum by terminal cuttings taken at Rijnsburg, The Netherlands, has shown that the unique features of this new Hypericum are stable and reproduced true to type in successive generations of asexual reproduction.

SUMMARY OF THE INVENTION

The following traits have been repeatedly observed and are determined to be the unique characteristics of 'Bosaney'. These charateristics in combination distinguish 'Bosaney' as a new and distinct cultivar:

1. Medium to late flowering.
2. Long stem length.
3. Medium-sized light orange red-colored berries.
4. Excellent post-production longevity.

Compared to plants of the female parent, code number 93, which have light pink-colored berries, plants of the new Hypericum produce larger berries. Compared to plants of the male parent, code number 71, which have salmon-colored berries, plants of the new Hypericum produce smaller berries.

Plants of the new Hypericum can be compared to plants of the Hypericum cultivar 'Bosapin', disclosed in U.S. Plant Pat. No. 10,993. In side-by-side comparisons conducted in Rijnsburg, The Netherlands, plants of the new Hypericum have shorter leaves, smaller berries and have lighter colored berries than plants of the cultivar 'Bosapin'.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the actual colors of the new Hypericum.

The photograph on the first sheet comprises a top perspective view of a typical plant of 'Bosaney'.

The photograph at the top of the second sheet is a close-up view of a typical opened flower of 'Bosaney'.

The photograph at the bottom of the second sheet is a close-up view of typical berries of 'Bosaney'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The following observations and measurements describe plants grown in Rijnsburg, The Netherlands, under outdoor commercial production practice planted in the field. Plants used for the description were about two years old. In the following description, color references are made to The Royal Horticultural Society Colour Chart except where general terms of ordinary dictionary significance are used.

Classification:

*Botanical.*—*Hypericum androsaemum* cultivar 'Bosaney'.

*Commercial.*—Cut flower Hypericum; no medicinal value.

Parentage:

*Female parent.*—Proprietary selection of *Hypericum androsaemum* code number 93, not patented.

*Male parent.*—Proprietary selection of *Hypericum androsaemum* code number 71, not patented.

Propagation:

*Type.*—Terminal cuttings.

Plant description:

*Plant form.*—Upright and broad woody shrub with erect lateral branches, branch angle about 45°.

*Growth habit.*—Moderately vigorous. Freely branching and dense growth.

*Plant height.*—About 70 cm.

*Plant width* (*spread*).—About 30 cm.

*Stem length.*—About 65 cm.

*Stem and lateral branch color.*—Young branches, light green, close to 144B, with relatively weak hint of red brown-colored anthocyanin.

*Foliage description.*—Leaves opposite; single; sessile and generally symmetrical. Length: About 8 cm. Width: About 5 cm. Shape: Ovate. Apex: Acute. Base: Obtuse. Margin: Entire. Texture: Smooth; leathery. Aspect: About 80° to stem. Color: Upper surface: 137A. Lower surface: 137C.

Flower description:

*Flower type and habit.*—Bright yellow flowers arranged in terminal compound umbels. Flowers not fragrant.

*Time to flower.*—Medium to late flowering; plants flower about 14 to 15 weeks after planting.

*Natural flowering season.*—Early autumn, typically August and September in The Netherlands.

*Post-production longevity.*—Cut flower are typically harvested when all flowers have developed berries. From flowers to berries takes about three weeks. Post-production longevity of cut stems is about 16 days.

*Flower diameter.*—About 2 cm.

*Petals.*—Quantity: Typically five per flower. Length: About 1.2 cm. Width: About 9 mm. Shape: Broadly elliptic to almost round; concave. Apex: Acute. Base: Attenuate. Margin: Entire. Color, both surfaces: 13A to 13B.

*Sepals.*—Quantity: Typically five per flower; three larger sepals and two smaller sepals. Shape: Broadly elliptic with nearly rounded apex. Orientation: Inner angle of about 70° to peduncle. Color, both surfaces: Green, 137B, red purple tint at margin.

*Peduncle.*—Strength: Strong. Length: About 1 cm. Aspect: Erect. Color: Light green, 143A.

*Reproductive organs.*—Stamens. Stamen shape: Slightly fan-shaped. Stamen color: Yellow, 14A. Anther color: Light yellow, 10C. Pistils: Quantity: Three per flower. Style color: Light yellow, 10C. Stigma color: Red purple, 185B. Ovary color: Light yellow, 10D.

*Fruit description.*—Type: Capsule, pyxis. Shape: Ellipsoidal. Length: About 1.2 cm. Diameter: About 8 mm. Color: Light orange red, between 39A and 41C, on a cream-colored, close to 11D, background, most noticeable at the base.

Disease resistance: Resistance to pathogens common to Hypericums has not been observed on plants grown under commercial conditions.

It is claimed:

1. A new and distinct cultivar of Hypericum plant named 'Bosaney', as illustrated and described.

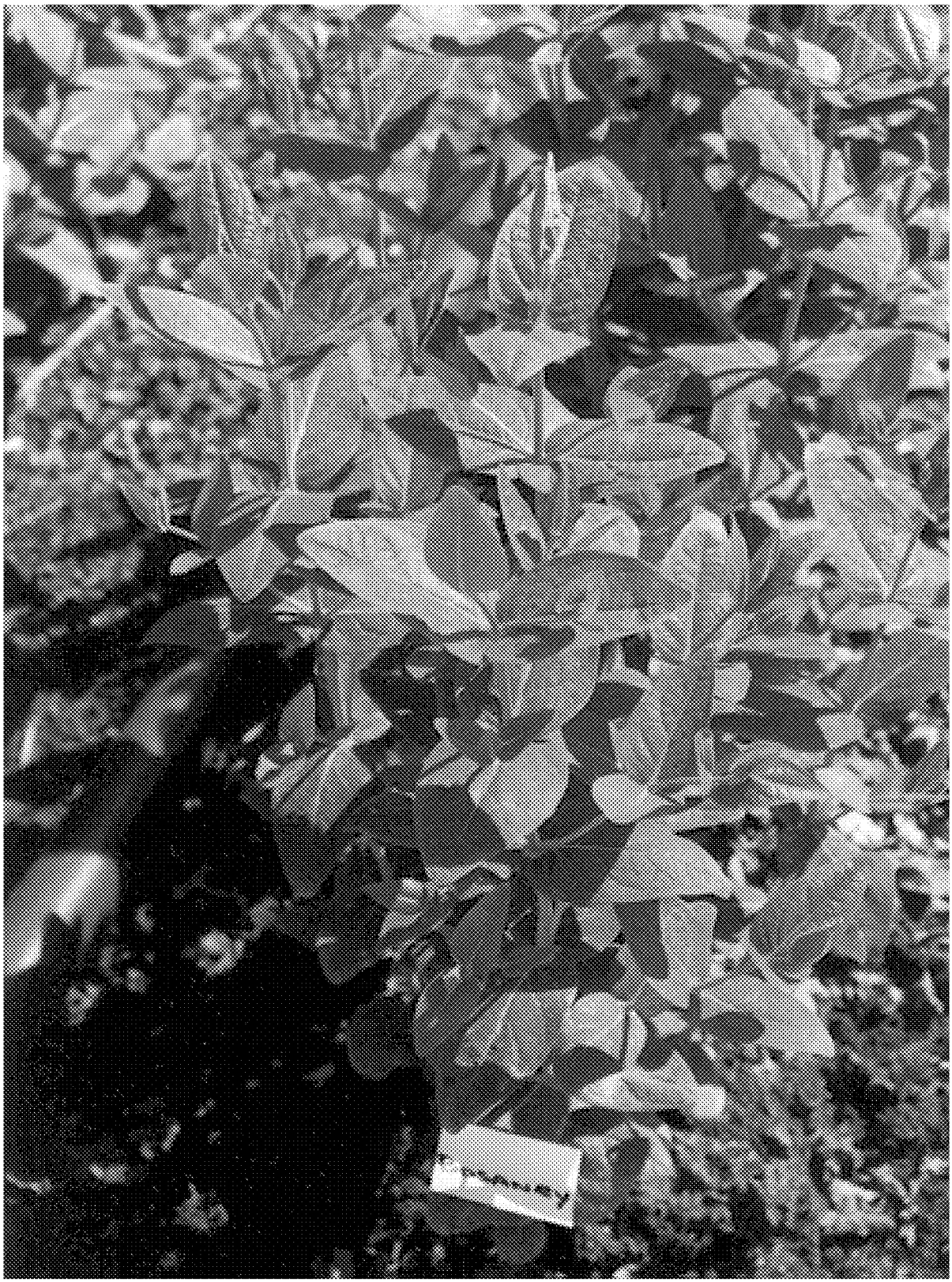

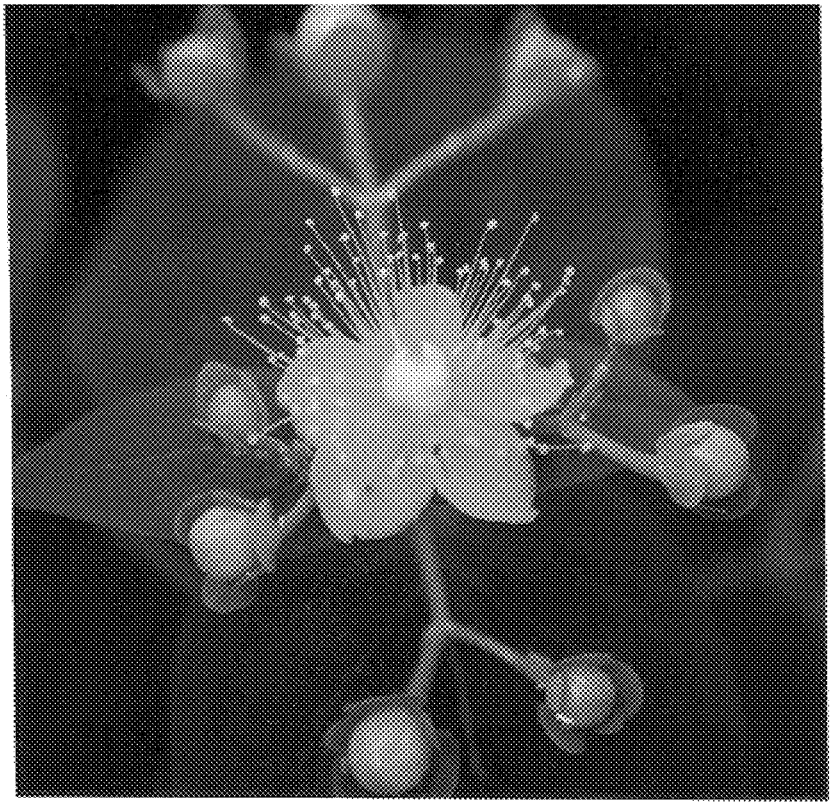
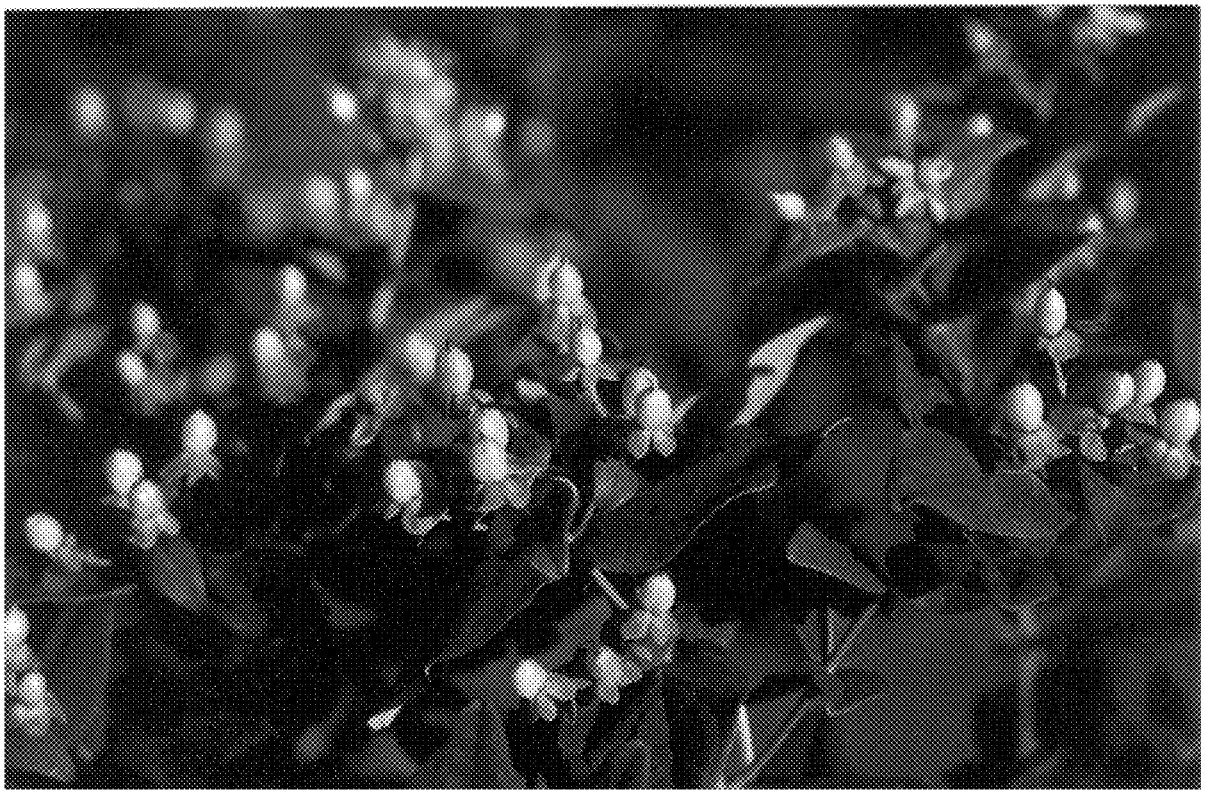

* * * * *